US00RE41184E

(19) United States
(12) Reissued Patent
Ito et al.

(10) Patent Number: US RE41,184 E
(45) Date of Reissued Patent: *Mar. 30, 2010

(54) PROCESS FOR PRODUCING A FLUORINE ATOM-CONTAINING SULFONYL FLUORIDE COMPOUND

(75) Inventors: Masahiro Ito, Yokohama (JP); Kunio Watanabe, Yokohama (JP); Takashi Okazoe, Yokohama (JP); Isamu Kaneko, Yokohama (JP); Daisuke Shirakawa, Yokohama (JP)

(73) Assignee: Asahi Glass Company, Limited, Tokyo (JP)

( * ) Notice: This patent is subject to a terminal disclaimer.

(21) Appl. No.: 12/234,109

(22) Filed: Sep. 19, 2008

Related U.S. Patent Documents

Reissue of:
(64) Patent No.: 7,105,697
Issued: Sep. 12, 2006
Appl. No.: 10/808,274
Filed: Mar. 25, 2004

U.S. Applications:

(62) Division of application No. 11/812,533, filed on Jun. 19, 2007, which is a division of application No. 10/442,227, filed on May 21, 2003, now Pat. No. 6,790,982, which is a continuation of application No. PCT/JP01/10407, filed on Nov. 28, 2001.

(30) Foreign Application Priority Data

Nov. 28, 2000 (JP) ..... 2000-361450

(51) Int. Cl.
*C07C 69/66* (2006.01)
*C07C 69/63* (2006.01)
*C07C 309/00* (2006.01)

(52) U.S. Cl. ..... 560/184; 560/227; 562/824; 562/825

(58) Field of Classification Search ..... None
See application file for complete search history.

(56) References Cited

U.S. PATENT DOCUMENTS

| | | | |
|---|---|---|---|
| 3,900,372 | A | 8/1975 | Childs et al. |
| 4,524,032 | A | 6/1985 | Misaki et al. |
| 4,868,318 | A | 9/1989 | Scherer, Jr. et al. |
| 4,996,369 | A | 2/1991 | Kalota et al. |
| 5,093,432 | A | 3/1992 | Bierschenk et al. |
| 5,322,903 | A | 6/1994 | Bierschenk et al. |
| 5,466,877 | A | 11/1995 | Moore |
| 5,488,142 | A | 1/1996 | Fall et al. |
| 5,571,870 | A | 11/1996 | Bierschenk et al. |
| 5,578,278 | A | 11/1996 | Fall et al. |
| 5,674,949 | A | 10/1997 | Bierschenk et al. |
| 5,753,776 | A | 5/1998 | Bierschenk et al. |
| 6,093,860 | A | 7/2000 | Watanabe et al. |
| 6,255,536 | B1 | 7/2001 | Worm et al. |
| 6,586,626 | B2 | 7/2003 | Okazoe et al. |
| 6,790,982 | B2 | 9/2004 | Ito et al. |
| 7,105,697 | B2 | 9/2006 | Ito et al. |
| 7,271,229 | B2 | 9/2007 | Okazoe et al. |
| 2004/0181091 | A1 * | 9/2004 | Ito et al. |

FOREIGN PATENT DOCUMENTS

| | | |
|---|---|---|
| EP | 0 062 430 | 10/1982 |
| EP | 0 265 052 | 4/1988 |
| JP | 52-10221 | 1/1977 |
| JP | 10-116627 | 5/1998 |
| WO | 00/56694 | 9/2000 |
| WO | 01/46107 | 6/2001 |
| WO | 02/10107 | 2/2002 |

OTHER PUBLICATIONS

Murata, K., et al., J. Am. Chem. Soc., vol. 120, No. 28, pp. 7117–7118, "The Thermal Decomposition of Perfluoroesters," 1998.
Tari, I, et al., J. Org. Chem., vol. 45, No. 7, pp. 1214–1217, "Synthesis of Halogenated Esters of Fluorinated Carboxylic Acids by the Regio–and Streospecific Addition of Acyl Hypochlorites to Olefins," 1980.
English Abstracts of WO 01/16085, Mar. 8, 2001.
English Abstracts of WO 01/46093, Jun. 28, 2001.
English Abstracts of WO 01/94285, Dec. 13, 2001.
English Abstracts of WO 02/04397, Jan. 17, 2002.
English Abstracts of WO 02/10106, Feb. 7, 2002.
English Abstracts of WO 02/10108, Feb. 7, 2002.
English Abstracts of WO 02/18314, Mar. 7, 2002.
English Abstracts of WO 02/20445, Mar. 14, 2002.
English Abstracts of WO 02/26679, Apr. 4, 2002.
English Abstracts of WO 02/26682, Apr. 4, 2002.
English Abstracts of WO 02/26686, Apr. 4, 2002.
English Abstracts of WO 02/26687, Apr. 4, 2002.
English Abstracts of WO 02/26688, Apr. 4, 2002.
English Abstracts of WO 02/26689, Apr. 4, 2002.
English Abstracts of WO 02/26693, Apr. 4, 2002.

(Continued)

*Primary Examiner*—Paul A Zucker
(74) *Attorney, Agent, or Firm*—Oblon, Spivak, McClelland, Maier & Neustadt, L.L.P.

(57) ABSTRACT

The present invention provides a process whereby fluorine atom-containing sulfonyl fluoride compound(s) useful as e.g. materials for ion-exchange membranes, can be produced efficiently and at low cost without structural limitations while solving the difficulties in production. Namely, the present invention provides a process which comprises reacting $XSO_2R^A$-$E^1$ (1) with $R^B$-$E^2$ (2) to form $XSO_2R^A$-E-$R^B$ (3), then reacting (3) with fluorine in a liquid phase to form $FSO_2R^{AF}$-$E^F$-$R^{BF}$ (4), and further, decomposing the compound to obtain $FSO_2R^{AF}$-$E^{F1}$ (5), wherein $R^A$ is a bivalent organic group, $E^1$ is a monovalent reactive group, $R^B$ is a monovalent organic group, $E^2$ is a monovalent reactive group which is reactive with $E^1$, E is a bivalent connecting group formed by the reaction of $E^1$ with $E^2$, $R^{AF}$ is a bivalent organic group formed by the fluorination of $R^A$, etc., $R^{BF}$ is the same group as $R^B$, etc., $E^F$ is a bivalent connecting group formed by the fluorination of E, etc., $E^{F1}$ is a monovalent group formed by the decomposition of $E^F$, and X is a halogen atom.

4 Claims, No Drawings

OTHER PUBLICATIONS

James J. Krutak, et al., "Chemistry of Ethenesulfonyl Fluoride. Flurosulfonylethylation of Organic Compounds," J. Org. Chem., vol. 44, No. 22, 1979, pp. 3847–3858.

Methods of Organic Chemistry, 4, vol. 10b, Part 1, pp. 703.

U.S. Appl. No. 10/808,274, filed Mar. 25, 2004, Ito et al.*

U.S. Appl. No. 10/830,140, filed Apr. 23, 2004, Okazoe et al.*

U.S. Appl. No. 10/421,924, filed Apr. 24, 2003, Okazoe et al.*

U.S. Appl. No. 11/318,978, filed Dec. 28, 2005, Murata et al.*

U.S. Appl. No. 11/322,396, filed Jan. 3, 2006, Murata et al.*

* cited by examiner

PROCESS FOR PRODUCING A FLUORINE ATOM-CONTAINING SULFONYL FLUORIDE COMPOUND

Matter enclosed in heavy brackets [ ] appears in the original patent but forms no part of this reissue specification; matter printed in italics indicates the additions made by reissue.

CROSS-RELATED APPLICATIONS

[This application is a Divisional Application of 10/442,227, filed May 21, 2003, now U.S. Pat. No. 6,790,982 which is a continuation of PCT/JP01/10407, filed on November 28, 2001.]

*More than one reissue application has been filed for the reissue of U.S. Pat. No. 7,105,697. The reissue applications are U.S. application Ser. No. 11/812,533 (the parent reissue application), U.S. Ser. No. 12/234,109 (the present application), and U.S. Ser. No. 12/234,140. U.S. Ser. No. 12/234,109 and U.S. Ser. No. 12/234,140 are divisional reissues of U.S. Pat. No. 7,105,697 and were filed based on U.S. Ser. No. 11/812,533, the parent broadening reissue application of U.S. Pat. No. 7,105,697.*

TECHNICAL FIELD

The present invention relates to a process for producing fluorine atom-containing sulfonyl fluoride compounds useful as e.g. materials for ion-exchange resins, and novel chemical substances useful as intermediates in the process.

BACKGROUND ART

Fluorine atom-containing sulfonyl fluoride compounds having a fluoroformyl group (such as the following compound (i)) are useful as materials for ion-exchange resins. Heretofore, compounds having a fluoroformyl group have been synthesized by a process which comprises reacting perfluoroalkylene oxides to a cyclic compound obtainable by the reaction of tetrafluoroethylene with sulfur trioxide ($SO_3$). for example, the following compound (i) can be obtained by reacting hexafluoropropylene oxide (HFPO) to the above-mentioned cyclic compound, as shown by the following formula.

(i)

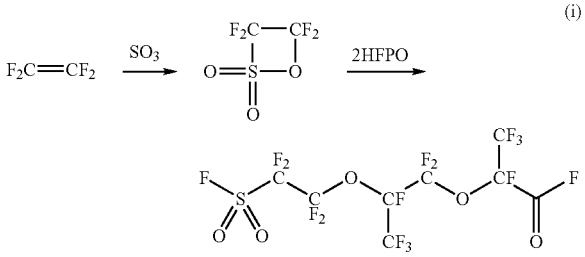

However, the conventional synthetic process was a disadvantageous process for practical industrial application, since a due care is required for handling $SO_3$. Further, reduction of the price can hardly be accomplished because the difficulty in synthesis is high. In addition, the obtainable compound (i) is limited to a compound having a side chain (—$CF_3$), whereby there has been a problem from the viewpoint of the membrane characteristics of the ion-exchange membrane prepared from a derivative of the compound (i).

The present invention has been made for the purpose of solving the problems of the prior art and provides a process which solves the difficulty in production and whereby fluorosulfonyl fluoride compounds having various molecular structures can be produced efficiently and at low costs.

DISCLOSURE OF THE INVENTION

The present inventors have invented a process which comprises reacting a sulfonyl halide compound having a certain specific structure with fluorine in a liquid phase, followed by decomposition of the product, and have found it possible to thereby carry out a process for producing the desired fluorine atom-containing sulfonyl fluoride compounds.

Namely, the present invention provides a process for producing fluorine atom-containing sulfonyl fluoride compounds, which comprises reacting a compound of the following formula (1) with a compound of the following formula (2) to form a compound of the formula (3), then, reacting the compound of the formula (3) with fluorine in a liquid phase to form a compound of the following formula (4), and further, decomposing the compound of the formula (4) to obtain a compound of the following formula (5):

$$XSO_2R^A\text{-}E^1 \quad (1)$$

$$R^B\text{-}E^2 \quad (2)$$

$$XSO_2R^A\text{-}E\text{-}R^B \quad (3)$$

$$FSO_2R^{AF}\text{-}E^F\text{-}R^{BF} \quad (4)$$

$$FSO_2R^{AF}\text{-}E^{F1} \quad (5)$$

wherein $R^A$ is a bivalent organic group, $E^1$ is a monovalent reactive group, $R^B$ is a monovalent organic group, $E^2$ is a monovalent reactive group which is reactive with $E^1$, E is a bivalent connecting group formed by the reaction of $E^1$ with $E^2$, $R^{AF}$ is the same group as $R^A$, or a bivalent organic group formed by the fluorination of $R^A$, $R^{BF}$ is the same group as $R^B$, or a monovalent organic group formed by the fluorination of $R^B$, $E^F$ is the same group as E, or a bivalent connecting group formed by the fluorination of E, $E^{F1}$ is a monovalent group formed by the decomposition of $E^F$ and X is a halogen atom, provided that at least one of $R^A$, $R^B$ and E is a group which can be fluorinated, and at least one of $R_{AF}$, $R^{BF}$ and $E^F$ is a group formed by the fluorination of $R^A$, $R^B$ and E, respectively.

Further, the present invention provides the above process, wherein the compound of the formula (4) is decomposed to obtain not only the compound of the formula (5), but also a compound of the following formula (6):

$$R^{BF}\text{-}E^{F2} \quad (6)$$

wherein $E^{F2}$ is a monovalent group formed by the decomposition of $E^F$, which may be the same as or different from $E^{F1}$, and $R^{BF}$ is as defined above.

Further, the present invention provides the above process, wherein the compound of the formula (1) is a compound of the following formula (1a), the compound of the formula (2) is a compound of the following formula (2a), the compound of the formula (3) is a compound of the following formula (3a), the compound of the formula (4) is a compound of the following formula (4a), and the compound of the formula (5a) is a compound of the following formula (5a):

$$XSO_2R^A\text{—}CH_2OH \quad (1a)$$

$$R^B\text{—}COY \quad (2a)$$

$$XSO_2R^A—CH_2OCO—R^B \quad (3a)$$

$$FSO_2R^{AF}—CF_2OCO—R^{BF} \quad (4a)$$

$$FSO_2R^{AF}—COF \quad (5a)$$

wherein Y is a halogen atom which is the same as or different from X, and $R^A$, $R^B$, $R^{AF}$ and $R^{BF}$ are as defined above.

Further, the present invention provides the above process, wherein the compound of the formula (4a) is decomposed to obtain not only the compound of the formula (5a), but also a compound of the following formula (6a):

$$R^{BF}—COF \quad (6a)$$

wherein $R^{BF}$ is as defined above.

Further, the present invention provides the above process, wherein the compound of the formula (2a) has the same structure as the compound of the formula (6a), and at least a part of the compound of the formula (6a) obtained from the reaction product obtained by the decomposition of the compound of the formula (4a), is used as at least a part of the compound of the formula (2a) to react with the compound of the formula (1a), to continuously obtain the compound of the formula (5a).

Further, the present invention provides a compound of the following formula (1) or a compound of the following formula (II):

$$FSO_2CH_2CH_2OCH_2CH_2OCOCF(CF_3)OCF_2CF_2CF_3 \quad (I)$$

$$FSO_2CF_2CF_2OCF_2CF_2OCOCF(CF_3)OCF_2CF_2CF_3 \quad (II)$$

BEST MODE FOR CARRYING OUT THE INVENTION

In this specification, the compound of the formula (1) will be referred to as "the compound 1". The, compounds of other formulae will be referred to in the same manner.

In the present invention, $R^A$ is a bivalent organic group, $R^B$ is a monovalent organic group, $R^{AF}$ is the same group as $R^A$ or a bivalent group formed by the fluorination of $R^A$, and $R^{BF}$ is the same group as $R^B$ or a monovalent organic group formed by the fluorination of $R^B$.

In this specification, "an organic group" means a group containing at least one carbon atom. A "halogeno" group means a group having at least one hydrogen atom bonded to a carbon atom substituted by a halogen atom. A "perhalogeno" group means a group having substantially all of hydrogen atoms bonded to carbon atoms substituted by halogen atoms. A "partially halogeno" group means a group having some of hydrogen atoms bonded to carbon atoms substituted by halogen atoms. In a case where halogen atoms are specified to be fluorine atoms, they may be referred to as "perfluoro", "partially fluoro", etc. The same applies with respect to other halogen atoms. A "perhalogeno" group and a "partially halogeno" group may be ones containing one type of halogen atoms or two or more types of halogen atoms.

A "perhalogeno" group is preferably a group having all of hydrogen atoms bonded to carbon atoms substituted by halogen atoms. However, even when unsubstituted hydrogen atoms remain, so long as-the nature as a group is substantially equal to a "perhalogeno" group, such a group will be included in the concept of the "perhalogeno" group in the present invention.

In the present invention, the "fluorination" means to introduce fluorine atoms into a compound. Specifically, it means that an organic group is converted to a perfluoro group or a partially fluoro group. The fluorination is carried out usually by substituting fluorine atoms for hydrogen atoms bonded to carbon atoms. In a case where an unsaturated bond is contained in an organic group, fluorine atoms will be added to the unsaturated bond by the fluorination.

In the present invention, a "saturated" group means a group wherein carbon-carbon bonds are solely single bonds, and so long as carbon-carbon bonds are single bonds, an unsaturated bond such as C═O or $SO_2$ may, for example, be present in the group.

In the present invention, a "hetero atom-containing" group means a group containing hetero atom(s) such as oxygen atom(s), nitrogen atom(s) or sulfur atom(s), or hetero atom group(s) such as —C—C(═O)—C— or —C—$SO_2$—C—. The hetero atom-containing group is preferred, if it is a group which is not easily decomposed by heating. From this viewpoint, the hetero atom-containing group is preferably a group containing etheric oxygen atom(s) (—O—) or ═O, particularly preferably a group containing etheric oxygen atom(s).

$R^A$ (the bivalent organic group) is preferably a bivalent hydrocarbon group, a halogeno bivalent hydrocarbon group, a hetero atom-containing bivalent hydrocarbon group, a halogeno(hetero atom-containing bivalent hydrocarbon) group. The bivalent hydrocarbon group may be a bivalent aliphatic hydrocarbon group, a bivalent aromatic hydrocarbon group or a bivalent alicyclic hydrocarbon group, and preferred is a bivalent aliphatic hydrocarbon group. In the bivalent aliphatic hydrocarbon group, single bond(s), double bond(s) or triple bond(s) may be present (or coexistent), as carbon-carbon bond(s). Further, the bivalent aliphatic hydrocarbon group may be of any structure such as a linear structure, a branched structure, a cyclic structure or a structure partially having a cyclic structure.

$R^A$ is preferably a bivalent organic group having hydrogen atoms bonded to carbon atoms. It is more preferably a bivalent saturated hydrocarbon group, a partially halogeno bivalent saturated hydrocarbon group, a hetero atom-containing bivalent saturated hydrocarbon group or a partially halogeno (hetero atom-containing bivalent saturated hydrocarbon) group, particularly preferably a bivalent saturated hydrocarbon group, or a hetero atom-containing bivalent saturated hydrocarbon group.

When $R^A$ is a bivalent saturated hydrocarbon group, an alkylene group, a cycloalkylene group or a cycloalkylalkylene group may be mentioned. As the alkylene group, a $C_{1-10}$ alkylene group is preferred. As the cycloalkylene group, a 3- to 6-membered cycloalkylene group or a group having at least one hydrogen atom of such a cycloalkylene group substituted by an alkyl group, is preferred. As the cycloalkylalkylene group, one hydrogen atom of a $C_{1-3}$ alkyl group substituted by the above-mentioned cycloalkyl group, is preferred.

When $R^A$ is a partially halogeno bivalent saturated hydrocarbon group, it may be a group having the above-mentioned bivalent saturated hydrocarbon group partially halogenated. The partially halogeno bivalent saturated hydrocarbon group may be of a linear structure or a branched structure, or may partially have a cyclic structure, and a partially fluoroalkylene group or a partially fluoro(partially chloroalkylene) group is preferred. The carbon number of the partially halogeno bivalent saturated hydrocarbon group is preferably from 1 to 20.

When $R^A$ is a hetero atom-containing bivalent saturated hydrocarbon group, it may be a group having a bivalent hetero atom or a bivalent hetero atom group inserted between the carbon-carbon atoms in the above bivalent saturated hydrocarbon group, or a group having hetero atoms bonded to carbon atoms of the above-mentioned bivalent saturated hydrocarbon group, or a group having bivalent hetero atoms or bivalent hetero atom groups bonded to carbon atoms at the bond terminals of the above bivalent saturated hydrocarbon group. The hetero atom-containing bivalent saturated hydrocarbon group is preferably a $C_{1-20}$ group. From the usefulness of the compounds, an etheric oxygen atom-containing bivalent saturated hydrocarbon group is preferred, as an etheric oxygen atom-containing alkylene group is particularly preferred.

When $R^A$ is a partially halogeno(hetero atom-containing bivalent saturated hydrocarbon) group, it may be a group having the above-mentioned hetero atom-containing bivalent saturated hydrocarbon group partially halogenated. The partially halogeno(hetero atom-containing bivalent saturated hydrocarbon) group may be of a linear structure or a branched structure, or may have a partially cyclic structure. A partially fluoro(hetero atom-containing bivalent hydrocarbon) group or a partially fluoro(partially chloro (hetero atom-containing bivalent hydrocarbon)) group is preferred. The carbon number of the partially halogeno (hetero atom-containing bivalent saturated hydrocarbon) group is preferably from 1 to 20.

$R^B$ (the monovalent organic group) is preferably a monovalent hydrocarbon group, a halogeno monovalent hydrocarbon group, a hetero atom-containing monovalent hydrocarbon group, or a halogeno(hetero atom-containing monovalent hydrocarbon) group. The monovalent hydrocarbon group may be a monovalent aliphatic hydrocarbon group, a monovalent aromatic hydrocarbon group, or a monovalent alicyclic hydrocarbon group, and a monovalent aliphatic hydrocarbon group is preferred. In the monovalent aliphatic hydrocarbon group, a single bond, a double bond, or a triple bond may be present (or coexistent) as a carbon-carbon bond. Further, the monovalent aliphatic hydrocarbon group may be of a linear structure, a branched structure, a cyclic structure, or a structure partially having a cyclic structure.

$R^B$ is preferably a saturated group. When $R^B$ is a monovalent saturated hydrocarbon group, it may be an alkyl group, a cycloalkyl group, or a cycloalkylalkyl group. The alkyl group is preferably a $C_{1-10}$ alkyl group. The cycloalkyl group is preferably a 3- to 6-membered cycloalkyl group or a group having at least one hydrogen atom of such a cycloalkyl group substituted by an alkyl group. The cycloalkylalkyl group is preferably a group having one of hydrogen atoms of a $C_{1-3}$ alkyl group substituted by the above cycloalkyl group.

When $R^B$ is a partially halogeno monovalent saturated hydrocarbon group, it may be a group having the above monovalent saturated hydrocarbon group partially halogenated. The partially halogeno monovalent saturated hydrocarbon group may be of a linear structure or a branched structure, or may have a partially cyclic structure, and a partially fluoroalkyl group or a partially fluoro(partially chloro alkyl) group is preferred. The carbon number of the partially halogeno monovalent hydrocarbon group is preferably from 1 to 20.

When $R^B$ is a hetero atom-containing monovalent saturated hydrocarbon group, it is preferably a group having a bivalent hetero atom or a bivalent hetero atom group inserted between the carbon-carbon atoms in the above monovalent saturated hydrocarbon group, or a group having a hetero atom bonded to a carbon atom in the above monovalent saturated hydrocarbon group, or a group having a bivalent hetero atom or a bivalent hetero atom group bonded to a carbon atom at the bond terminal of the above monovalent saturated hydrocarbon group. The hetero atom-containing monovalent saturated hydrocarbon group is preferably a group having a carbon number of from 1 to 20. In view of the availability, the production efficiency and the usefulness of the formed product, an etheric oxygen atom-containing alkyl group is preferred, and an alkoxyalkyl group or an alkoxyl group is particularly preferred.

When $R^B$ is a partially halogeno(hetero atom-containing monovalent hydrocarbon) group, it may be a group having the above hetero atom-containing monovalent saturated hydrocarbon group partially halogenated. The partially halogeno(hetero atom-containing monovalent saturated hydrocarbon) group may be of a linear structure or a branched structure, or may partially have a cyclic structure, and a partially fluoro(hetero atom-containing monovalent hydrocarbon) group or a partially fluoro(partially chloro (hetero atom-containing monovalent hydrocarbon)) group is preferred. The carbon number of the partially halogeno (hetero atom-containing monovalent saturated hydrocarbon) group is preferably from 1 to 20.

$R^{AF}$ is the same group as $R^A$, or a bivalent organic group formed by the fluorination of $R^A$. $R^{AF}$ is the same group as $R^A$ in a case where $R^A$ is a group which can not be fluorinated, or in a case where $R^A$ is not fluorinated, even if it is a group which can be fluorinated. For example, in a case where $R^A$ is a perhalogeno bivalent hydrocarbon group or a perhalogeno(hetero atom-containing bivalent hydrocarbon) group, the halogen atoms in such a group will not be changed even if reacted with fluorine in a liquid phase, and therefore, $R^{AF}$ will be the same group as $R^A$, $R^{BF}$ is the same group as $R^B$, or a group formed by the fluorination of $R^B$. $R^{BF}$ is the same group as $R^B$ in a case where $R^B$ is a group which can not be fluorinated, or in a case where $R^B$ is not fluorinated even if it is a group which can be fluorinated. For example, in a case where $R^B$ is a perhalogeno monovalent hydrocarbon group or a perhalogeno(hetero atom-containing monovalent hydrocarbon) group, the halogen atoms in such a group will not be changed even if reacted with fluorine in a liquid phase, and therefore, $R^{BF}$ will be the same group as $R^B$.

$R^{AF}$ is preferably a perfluoro bivalent saturated hydrocarbon group, a perfluoro(partially halogeno bivalent saturated hydrocarbon) group, a perfluoro(hetero atom-containing bivalent saturated hydrocarbon) group, or a perfluoro (partially halogeno(hetero atom-containing bivalent saturated hydrocarbon)) group. $R^A$ in such a case is preferably a bivalent saturated hydrocarbon group, a partially halogeno bivalent saturated hydrocarbon group, a hetero atom-containing bivalent saturated hydrocarbon) group, or a partially halogeno(hetero atom-containing bivalent saturated hydrocarbon) group, which has the same number of carbon atoms as $R^{AF}$ and has a carbon skeleton structure corresponding to $R^{AF}$. Such a group may be a saturated group, or a group containing at least one carbon-carbon double bond and/or triple bond (hereinafter referred to simply as "an unsaturated group").

Further, $R^{BF}$ is preferably a perfluoro monovalent saturated hydrocarbon group, a perfluoro(partially halogeno monovalent saturated hydrocarbon) group, a perfluoro (hetero atom-containing monovalent saturated hydrocarbon) group, or a perfluoro(partially halogeno(hetero atom-containing monovalent saturated hydrocarbon)) group. $R^B$ is not particularly limited so long as it can be converted to $R^{BF}$ by a fluorination reaction, and it is particularly preferably the same group as $R^{BF}$, since the after-described fluorination reaction can thereby be carried out easily, and a continuous process can be carried out. Namely, $R^B$ is preferably a perfluoro monovalent saturated hydrocarbon group, a perfluoro (partially halogeno monovalent saturated hydrocarbon) group, a perfluoro(hetero atom-containing monovalent saturated hydrocarbon) group, or a perfluoro(partially halogeno (hetero atom-containing monovalent saturated hydrocarbon)) group.

$E^1$ is a monovalent reactive group, $E^2$ is a monovalent reactive group which is reactive with $E^1$, E is a bivalent connecting group formed by the reaction of $E^1$ with $E^2$, $E^F$ is the same group as E, or a bivalent connecting group formed by the fluorination of E, and $E^{F1}$ is a monovalent group formed by the decomposition of $E^F$. As a case where $E^F$ is the same group as E, a case may, for example, be mentioned where E is a perhalogeno bivalent connecting group. $E^2$ is preferably a group which is readily reactive with $E^1$ rather than with $XSO_2$— in the compound 1. Particularly preferably, $E^2$ is a group capable of reacting with $E^1$ without reacting with $XSO_2$—.

$E^1$ and $E^2$ are not particularly limited. For example, E to be formed is —$CH_2OCO$— (or —$COOCH_2$—) in a case where either one of $E^1$ and $E^2$ is —COZ (Z is a halogen atom), and the other is —$CH_2OH$. This E is reacted with fluorine in a liquid phase to form —$CF_2OCO$— (or —$COOCF_2$—) as $E^F$. Further, by decomposition of this $E^F$, —COF will be formed as $E^{F1}$. In the present invention, it is preferred that the compound 4 is decomposed to obtain not only the compound 5 but also the compound 6 represented by $R^{BF}$-$E^{F2}$. When $E^1$ and $E^2$ are the above groups, $E^{F2}$ will also be —COF (i.e. the same group as $E^{F1}$).

The compounds 1 to 5 are preferably compounds 1a to 5a, respectively. The compounds 1a to 5a are cases where $E^1$ is —$CH_2OH$, $E^2$ is —COY (Y is a halogen atom), E is —$CH_2OCO$—, $E^F$ is —$CF_2OCO$—, and $E^{F1}$ is —COF. Accordingly, the compound obtainable together with the compound 5a by the decomposition of the compound 4a, will be the compound 6a represented by $R^{BF}$—COF.

In the present invention, the fluorine content of the compound 3 is preferably at least 30 mass %. If the fluorine content of the compound 3 is less than 30 mass %, the solubility in the liquid phase at the time of the fluorination reaction, tends to be inadequate. The fluorine content of the compound 3 may be suitably adjusted to be at least 30% depending upon the type of the liquid phase for the fluorination reaction. However, the fluorine content is more preferably from 30 to 86 mass %, still further preferably from 30 to 76 mass %. It is economically disadvantageous to employ the compound 3 having a fluorine content exceeding 86 mass %, and the available compound tends to be limited in such a case.

Further, the molecular weight of the compound 3 is preferably from 200 to 1,000. If the molecular weight of the compound 3 is less than 200, the boiling point of the compound 3 tends to be low, and the compound 3 is likely to evaporate during the process of fluorination, whereby the yield of the fluorinated product tends to be low. Further, a decomposition reaction may also take place. On the other hand, if the molecular weight exceeds 1,000, the solubility in the liquid phase tends to be low, and the purification tends to be difficult.

In the present invention, X is preferably a fluorine atom. When X is a fluorine atom, there is a merit that the yield of the fluorination reaction will be remarkably improved as compared with a case where X is other halogen atom. Further, in the present invention, also Y is preferably a fluorine atom.

Further, at least one of the above $R^A$, $R^B$ and E is a group which can be fluorinated, and at least one of $R^{AF}$, $R^{BF}$ and $E^F$ is a group formed by the fluorination of $R^A$, $R^B$ and E, respectively.

A preferred embodiment of the present invention is a process wherein the compound 1a is reacted with the compound 2a to form the compound 3a (hereinafter referred to as "the esterification step"), then, the compound 3a is reacted with fluorine in a liquid phase to form the compound 4a (hereinafter referred to as "the fluorination step"), and further, the compound 4a is decomposed to obtain the following compound 5a (hereinafter referred to as "decomposition step"). The respective reaction steps of tis process will be described in detail.

$XSO_2R^A$—$CH_2OH$ (1a)

$R^B$—COY (2a)

$XSO_2R^A$—$CH_2OCO$—$R^B$ (3a)

$FSO_2R^{AF}$—$CF_2OCO$—$R^{BF}$ (4a)

$FSO_2R^{AF}$—COF (5a)

Firstly, the esterification step will be described.

The reaction of the compound 1a with the compound 2a in the esterification step, can be carried out under the conditions for known esterification reactions. Such a reaction can be carried out in the presence of a solvent (hereinafter referred to as "the solvent 1"), but it is preferred to carry out the reaction in the absence of the solvent 1 from the viewpoint of the volume efficiency. When the solvent 1 is employed, it is preferably dichloromethane, chloroform, triethylamine or a solvent mixture of triethylamine and tetrahydrofuran. The amount of the solvent 1 to be used, is preferably from 50 to 500 mass %, based on the total amount of the compound 1a and the compound 2a.

By the reaction of the compound 1a with the compound 2a, an acid represented by HY will be formed. In a case where as the compound 2a, a compound wherein Y is a fluorine atom, is employed, HF will be formed. Therefore, as a scavenger for HF, an alkali metal fluoride (preferably NaF or KF) or a trialkylamine may be present in the reaction system. In a case where the compound 1a or the compound 2a is a compound unstable against an acid, it is preferred to use a scavenger for HF. Otherwise, in a case where no scavenger for HF is employed, it is preferred to discharge HF out of the reaction system, as carried by a nitrogen stream. When the alkali metal fluoride is employed, its amount is preferably from 1 to 10 times by mol, relative to the compound 2a.

The temperature for the reaction of a compound 1a with the compound 2a is preferably at least −50° C. and at most +100° C. or at most the boiling temperature of the solvent. Further, the reaction time for the reaction may suitably be changed depending upon the supply rate of the materials and the amounts of the compounds to be used for the reaction. The pressure for the reaction (the gauge pressure, the same applies hereinafter) is preferably from normal pressure to 2 MPa.

Further, as mentioned above, the molecular weight of the compound 3a is preferably from 200 to 1,000. Further, the fluorine content (the proportion of fluorine atoms in the molecule) of the compound 3a is preferably at least 30 mass %, more preferably from 30 to 86 mass %, still more preferably from 30 to 76 mass %.

A crude product containing the compound 3a formed by the reaction of the compound 1a with the compound 2a, may be purified depending upon the purpose, or may be used as it is for e.g. the next reaction. It is advisable to carry out the purification, so that the fluorination reaction in the next step can be proceeded smoothly.

The purification of the crude product may, for example, be a method of distilling the crude product as it is, a method of treating the crude product with a dilute alkali aqueous solution, followed by liquid separation, a method of extracting the crude product with a suitable organic solvent, followed by distillation, or silica gel column chromatography.

The following compounds may be mentioned as specific examples of the compound 1a.

$FSO_2CH_2CH_2OH$, $FSO_2CH_2CH_2OCH_2CH_2OH$, $FSO_2CH_2CH_2OCH_2CH_2OCH(CH_3)CH_2OH$.

The compound 1a is a compound which is readily available or which can easily be prepared by a known method. For example, $FSO_2CH_2CH_2OCH_2CH_2OH$ can be obtained by synthesizing 2-chloroethanesulfonyl fluoride and then reacting 2-chloroethanesulfonyl fluoride with ethylene glycol, by the method disclosed, for example, in J. Org. Chem., 44, 3847 (1979).

Further, the following compounds may be mentioned as specific examples of the compound 2a to be used in the esterification step.

$CF_3CF_2COF$, $CF_3CF_2CF_2OCF(CF_3)COF$, $CF_3CF_2CF_2OCF(CF_3)CF_2OCF(CF_3)COF$, $FSO_2CF_2COF$, $FSO_2CF_2CF_2OCF_2COF$, $FSO_2CF_2CF_2OCF_2CF_2OCF(CF_3)COF$.

The following compounds may be mentioned as specific examples of the compound 3a obtainable in the esterification step.

$FSO_2CH_2CH_2OCOCF_2CF_3$, $FSO_2CH_2CH_2OCOCF(CF_3)OCF_2CF_2CF_3$, $FSO_2CH_2CH_2OCOCF(CF_3)OCF_2CF(CF_3)OCF_2CF_2CF_3$, $FSO_2CH_2CH_2OCH_2CH_2OCOCF_2CF_3$, $FSO_2CH_2CH_2OCH_2CH_2OCOCF(CF_3)OCF_2CF_2CF_3$ (I), $FSO_2CH_2CH_2OCH_2CH_2OCOCF(CF_3)OCF_2CF(CF_3)OCF_2CF_2CF_3$, $FSO_2CH_2CH_2OCH_2CH_2OCH(CH_3)CH_2OCOCF_2CF_3$, $FSO_2CH_2CH_2OCH_2CH_2OCH(CH_3)CH_2OCOCF(CF_3)OCF_2CF_2CF_3$, $FSO_2CH_2CH_2OCH_2CH_2OCH(CH_3)CH_2OCOCF(CF_3)OCF_2CF(CF_3)OCF_2CF_2CF_3$, $FSO_2CH_2CH_2OCOCF_2SO_2F$, $FSO_2CH_2CH_2OCOCF_2OCF_2CF_2SO_2F$, $FSO_2CH_2CH_2OCOCF(CF_3)OCF_2CF_2OCF_2CF_2SO_2F$, $FSO_2CH_2CH_2OCH_2CH_2OCOCF_2SO_2F$, $FSO_2CH_2CH_2OCH_2CH_2OCOCF_2OCF_2CF_2SO_2F$, $FSO_2CH_2CH_2OCH_2CH_2OCOCF(CF_3)OCF_2CF_2OCF_2CF_2SO_2F$, $FSO_2CH_2CH_2OCH_2CH_2OCH(CH_3)CH_2OCOCF_2SO_2F$ $FSO_2CH_2CH_2OCH_2CH_2OCH(CH_3)CH_2OCOCF_2OCF_2CF_2SO_2F$, $FSO_2CH_2CH_2OCH_2CH_2OCH(CH_3)CH_2OCOCF(CF_3)OCF_2CF_2OCF_2CF_2SO_2F$.

The compound 3a may be led to a material for ion-exchange resins, by the reaction which will be described hereinafter. Further, the above compound 1 is a novel compound which is useful particularly in the case of producing a high performance fluororesin.

Now, the fluorination step will be described.

The fluorination reaction in the fluorination step is carried out in a liquid phase from the viewpoint of the yield and the operation efficiency of the reaction. Such a fluorination reaction may be carried out theoretically by an ECF method, a cobalt fluorination method, or a method of reaction with fluorine with a gas phase. However, from the viewpoint of the reaction yield and the efficiency in the reaction operation, fluorination in a liquid phase is a remarkably advantageous method.

The fluorination reaction is preferably carried out by a method wherein the compound 3a is reacted with fluorine ($F_2$) in the presence of a solvent (hereinafter referred to as "the solvent 2") to form the compound 4a. As the fluorine, fluorine gas may be employed as it is, or fluorine gas diluted with an inert gas may be employed. As such an inert gas, nitrogen gas or helium gas is preferred, and from the economical reason, nitrogen gas is particularly preferred. The amount of fluorine in nitrogen gas is not particularly limited, it is preferably at least 10 vol % from the viewpoint of efficiency, particularly preferably at least 20 vol %.

The solvent 2 is preferably a solvent which does not contain C—H bond(s) and which contains C—F bond(s) essentially. More preferred is a perfluoroalkane or an organic solvent obtained by perfluorinating a known organic solvent having in its structure at least one atom selected from the group consisting of a chlorine atom, a nitrogen atom, and an oxygen atom. Further, as the solvent 2, it is preferred to employ a solvent in which the solubility of the compound 3a is high, and it is particularly preferred to employ a solvent which is capable of dissolving at least 1 mass % of the compound 3a, especially preferred to employ a solvent capable of dissolving at least 5 mass % of the compound 3a.

Examples of the solvent 2 include the compound 4a in the case where it is a perfluorinated compound, a perfluoroalkane (tradename: FC-72, etc.), a perfluroether (FC-75, FC-77, etc.), a perfluoropolyether (tradename: KRYTOX, FOMBLIN, GALDEN, DEMNUM, etc.), a chlorofluorocarbon (tradename: FLON LUBE), a chlrofluoropolyether, a perfluoroalkylamine (such as a perfluorotrialkylamine), and an inert fluid (tradename: FLUORINERT). Among them, a perfluorotrialkylamine or the compound 4a in the case where it is a perfluorinated compound, is preferred. Especially when the compound 4a is employed, there is a merit that work up after the reaction will be easy. The amount of the solvent 2 is preferably at least five times by mass, particularly preferably from 10 to 100 times by mass, relative to the compound 3a.

The reaction system for the fluorination reaction may be a batch system or a continuous system. The continuous system may be the following continuous system 1 or 2, but from the viewpoint of the reaction yield and the selectivity, the continuous system 2 is preferred. Further, the fluorine gas may be one diluted with an inert gas such as a nitrogen gas in either case where the reaction is carried out in a batch system or in a continuous system.

Continuous System 1

A method wherein the compound 3a and the solvent 2 are charged into a reactor, and stirring is initiated to control the reaction temperature and the reaction pressure to prescribed levels, and then fluorine gas, or fluorine gas and the solvent 2, are continuously supplied for the reaction.

Continuous System 2

A method wherein the solvent 2 is charged into the reactor, and stirring is initiated to control the reaction temperature and the reaction pressure to prescribed levels, and then the compound 3a and fluorine gas are continuously and simultaneously supplied in a prescribed molar ratio.

In the continuous system 2, when the compound 3a is supplied, it is preferred to supply the compound 3a diluted with the solvent 2, whereby the selectivity can be improved, and the amount of by-products can be suppressed. Further, in the continuous system 2, when the compound 3a is diluted with the solvent, the amount of the solvent 2 to the compound 3a is preferably at least 5 times by mass, particularly preferably at least 10 times by mass.

With respect to the amount of fluorine to be used for the fluorination reaction, in either case where the reaction is carried out by a batch system or a continuous system, it is preferred that fluorine gas is present so that the amount of fluorine is always in excess equivalent to hydrogen atoms to be fluorinated, and it is particularly preferred to use fluorine gas so that it would be at least 1.5 times by equivalent (i.e. at least 1.5 times by mol) from the viewpoint of the selectivity. Further, the amount of fluorine gas is preferably maintained in an excess amount always from the initiation to the termination of the reaction.

The reaction temperature for the fluorination reaction is usually preferably at least −60° C. and at most the boiling point of the compound 3a, and from the viewpoint of the reaction yield, the selectivity and the efficiency for industrial operation, it is particularly preferably from −50° C. to +100° C., especially preferably from −20° C. to +50° C. The reaction pressure for the fluorination reaction is not particularly limited, and from the viewpoint of the reaction yield, the selectivity and the efficiency for industrial operation, it is particularly preferably from normal pressure to 2 MPa.

Further, in order to let the fluorination reaction proceed efficiently, it is preferred to add a C—H bond-containing compound to the reaction system at a later stage of the reaction or to carry out ultraviolet irradiation. For example, in a batch system reaction, it is preferred to add a C—H bond-containing compound to the reaction system at a later stage of the fluorination reaction, or to carry out ultraviolet irradiation, and in a continuous system reaction, it is preferred to supply a C—H bond-containing compound to the vicinity of the portion where the fluorination reaction product is withdrawn from the reaction apparatus, or, to irradiate ultraviolet rays. Thus, the compound 3a present in the reaction system can efficiently be fluorinated, whereby the conversion can remarkably be improved.

The C—H bond-containing compound may be an organic compound other than the compound 3a, and particularly preferred is an aromatic hydrocarbon. Benzene or toluene is, for example, particularly preferred. The amount of the C—H bond-containing compound is preferably from 0.1 to 10 mol %, particularly preferably from 0.1 to 5 mol %, based on hydrogen atoms in the compound 3a.

It is preferred to add the C—H bond-containing compound in a stage where fluorine gas is present in the reaction system. Further, in a case where the C—H bond-containing compound is added, it is preferred that the reaction system is pressurized. The pressure at the time of pressurizing is preferably from 0.01 to 5 MPa.

In a case where a reaction to substitute fluorine atoms for hydrogen atoms takes place in the reaction for fluorination of the compound 3a in a liquid phase, HF will be formed as a by-product. To remove the by-product HF, it is preferred to let a scavenger for HF be present in the reaction system or to contact the discharge gas with a HF scavenger at the gas outlet of the reactor. As the HF scavenger, the same one as described above may be employed, and NaF is preferred.

When the HF scavenger is permitted to be present in the reaction system, its amount is preferably from 1 to 20 times by mol, particularly preferably from 1 to 5 times by mol, based on the total amount of hydrogen atoms present in the compound 3a. In a case where the HF scavenger is placed at the gas outlet of the reactor, it is preferred that (1) a cooler, (which is preferably maintained at a level of from 10° C. to room temperature, particularly preferably at about 20° C.) (2) a packed layer of NaF pellets, and (3) a cooler (which is preferably maintained at a level of from −78° C. to +10° C., more preferably from −30° C. to 0° C.) are installed in series in the order of (1)-(2)-(3). Further, a liquid-returning line to return a condensed liquid from the cooler of (3) to the reactor, may be installed.

The crude product containing the compound 4a obtained in the fluorination step, may be employed as it is for the next step, or may be purified to one having high purity. As the purification method, a method of distilling the crude product as it is under normal pressure or reduced pressure may, for example, be mentioned.

The following compounds may be mentioned as specific examples of the compound 4a obtainable in the fluorination step.

$FSO_2CF_2CF_2OCOCF_2CF_3$,
$FSO_2CF_2CF_2OCOCF(CF_3)OCF_2CF_2CF_3$,
$FSO_2CF_2CF_2OCOCF(CF_3)OCF_2CF(CF_3)OCF_2CF_2CF_3$,
$FSO_2CF_2CF_2OCF_2CF_2OCOCF_2CF_3$,
$FSO_2CF_2CF_2OCF_2CF_2OCOCF(CF_3)OCF_2CF_2CF_3$ (II),
$FSO_2CF_2CF_2OCF_2CF_2OCOCF(CF_3)OCF_2CF(CF_3)OCF_2CF_2CF_3$,
$FSO_2CF_2CF_2OCF_2CF_2OCF(CF_3)CF_2OCOCF_2CF_3$,
$FSO_2CF_2CF_2OCF_2CF_2OCF(CF_3)CF_2OCOCF(CF_3)OCF_2CF_2CF_3$,
$FSO_2CF_2CF_2OCF_2CF_2OCF(CF_3)CF_2OCOCF(CF_3)OCF_2CF(CF_3)OCF_2CF_2CF_3$,
$FSO_2CF_2CF_2OCOCF_2SO_2F$,
$FSO_2CF_2CF_2OCOCF_2OCF_2CF_2SO_2F$,
$FSO_2CF_2CF_2OCOCF(CF_3)OCF_2CF_2OCF_2CF_2SO_2F$,
$FSO_2CF_2CF_2OCF_2CF_2OCOCF_2SO_2F$,
$FSO_2CF_2CF_2OCF_2CF_2OCOCF_2OCF_2CF_2SO_2F$,
$FSO_2CF_2CF_2OCF_2CF_2OCOCF(CF_3)OCF_2CF_2OCF_2CF_2SO_2F$,
$FSO_2CF_2CF_2OCF_2CF_2OCF(CF_3)CF_2OCOCF_2SO_2F$,
$FSO_2CF_2CF_2OCF_2CF_2OCF(CF_3)CF_2OCOCF_2OCF_2CF_2SO_2F$,
$FSO_2CF_2CF_2OCF_2CF_2OCF(CF_3)CF_2OCOCF(CF_3)OCF_2CF_2OCF_2CF_2SO_2F$.

Like the compound 3a, the compound 4a is also useful as an intermediate for a material for fluororesins and may be led to a material for ion-exchange resins by a reaction which will be described hereinafter. Further, the above compound II is a novel compound particularly useful in a case where a high performance fluororesin is to be produced.

Now, the decomposition step of decomposing the ester bond will be described.

The reaction in this decomposition step is carried out preferably by a pyrolytic reaction or a decomposition reaction which is carried out in the presence of a nucleophilic agent or an electrophilic agent.

The pyrolytic reaction can be carried out by heating the compound 4a. The reaction system for the pyrolytic reaction is preferably selected depending upon the boiling point and stability of the compound 4a. For example, in a case where a readily vaporizable compound 4a is to be pyrolized, it is possible to employ a gas phase pyrolytic method wherein the pyrolysis is continuously carried out in a gas phase, and a discharge gas containing the obtained compound 5a is condensed and recovered.

The reaction temperature in the gas phase pyrolytic method is preferably from 50 to 350° C., particularly preferably from 50 to 300° C., especially preferably from 150 to 250° C. Further, an inert gas which is not directly involved in the reaction, may also be present in the reaction system. As such an inert gas, nitrogen or carbon dioxide may, for example, be mentioned. Such an inert gas is preferably added in an amount of from 0.01 to 50 vol %, based on the compound 4a. If the amount of the added inert gas is large, the yield of the product may sometimes be reduced.

On the other hand, in a case where the compound 4a is a hardly vaporizable compound, it is preferred to employ a liquid phase pyrolytic method wherein it is heated in the state of a liquid in the reactor. The pressure for the reaction in this case is not particularly limited. In a usual case, the product containing the compound 5a has a lower boiling point, and therefore, it is preferred to obtain it: by a method of a reaction distillation system wherein the product is vaporized and continuously withdrawn. Otherwise, a method may be employed wherein after completion of the heating, the product is withdrawn all at once from the reactor. The reaction temperature in such a liquid phase pyrolytic method is preferably from 50 to 300° C., particularly preferably from 100 to 250° C.

In a case where pyrolysis is carried out by the liquid phase pyrolytic method, it may be carried out in the absence of any solvent or in the presence of a solvent (hereinafter referred to as "the solvent 3"). The solvent 3 is not particularly limited, so long as it is one which is not reactive with the compound 4a and is soluble in each other with the compound 4a and which is not reactive with the compound 5a to be formed. Further, as the solvent 3, it is preferred to select one which can readily be separated at the time of purification of the compound 5a. Specific examples of the solvent 3 include inert solvents such as perfluorotrialkylamine(s) and perfluoronaphthalene(s), and chlorotrifluoroethylene oligomer(s) (for example, tradename: FLON LUBE) having a high boiling point among the chlorofluoro-carbon(s), are preferred. Further, the amount of the solvent 3 is preferably from 10 to 1,000 mass %, based on the compound 4a.

Further, in the case where the compound 4a is reacted with a nucleophilic agent or an electrophilic agent in a liquid phase for decomposition, such a reaction may be carried out in the absence of any solvent or in the presence of a solvent (hereinafter referred to as "the solvent 4"). The solvent 4 is preferably the same as the solvent 3. The nucleophilic agent is preferably $F^-$, particularly preferably $F^-$ derived from an alkali metal fluoride. The alkali metal fluoride is preferably NaF, $NaHF_2$, KF or CsF. Among them, NaF or KF is particularly preferred from the viewpoint of the economical efficiency and the reactivity.

In a case where a nucleophilic agent (such as $F^-$) is employed, the nucleophilic agent to be used at the initial stage of the reaction may be in a catalytic amount or in an excess amount. The amount of the nucleophilic agent such as $F^-$ is preferably from 1 to 500 mol %, particularly preferably from 1 to 100 mol %, especially preferably from 5 to 50 mol %, based on the compound 4. The reaction temperature is preferably at a level of from −30° C. to the boiling point of the solvent or the compound 4a, particularly preferably from −20° C. to 250° C. This method is also preferably carried out in a reactor equipped with a distillation column.

The following compounds may be mentioned as specific examples of the compound 5a to be obtained in the decomposition step.

$FSO_2CF_2COF$, $FSO_2CF_2CF_2OCF_2COF$, $FSO_2CF_2CF_2OCF_2CF_2OCF(CF_3)COF$,

In the present invention, it is possible to obtain not only the compound 5a but also the following compound 6a by the decomposition of the compound 4a.

$R^{BF}$—COF (6a)

wherein $R^{BF}$ is as defined above.

In the present invention, it is preferred that the compound 2a has the same structure as the compound 6a. Namely, it is preferred that in the compound 2a, $R^B$ is $R^{BF}$, Y is F, and in the compound 3a, $R^B$ is $R^{BF}$. In such a case, it is possible to continuously obtain the compound 5a (continuous process) by employing at least a part of the compound 6a obtained from the reaction product obtained by the decomposition of the compound 4a, as at least a part of the compound 2a to react with the compound 1a. Further, when the compound 5a and the compound 6a have the same structure, the decomposition reaction product of the compound 4a can be used for the reaction with the compound 1a, without the necessity to separate the decomposition reaction product. The reaction scheme of the compound 1a, the compound 2a (=the compound 6a), and the compounds 3a to 6a, in such a case, may be represented by the following chemical formulae.

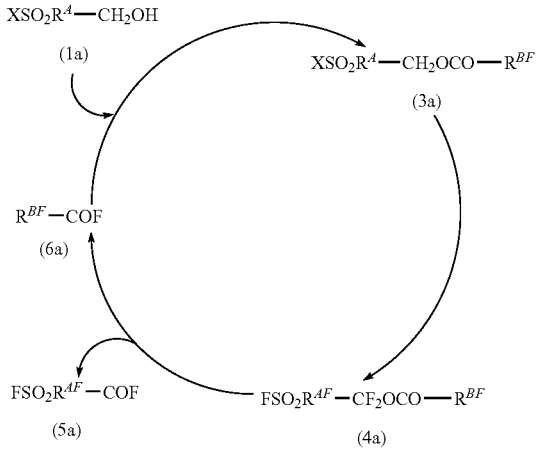

As one embodiment of the above continuous process, the following reactions employing compounds I to V may be mentioned. Namely, it is a continuous process wherein the following compound V is reacted with the following compound IV to form the following compound I, then, the compound I is reacted with fluorine in a liquid phase to form the following compound II, and further, the compound II is decomposed to obtain not only the following compound III but also the compound IV, and at least a part of the compound IV is reacted with the compound V. Here, the compounds I and II are the above-mentioned novel compounds.

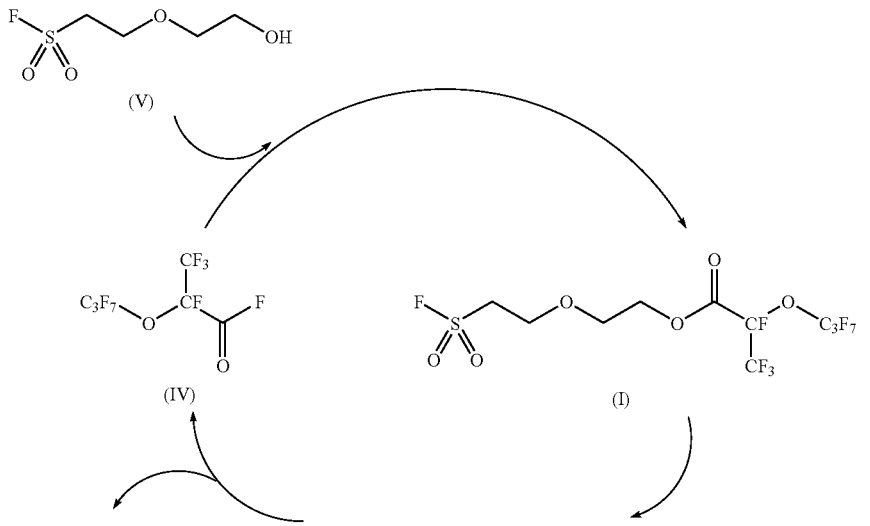

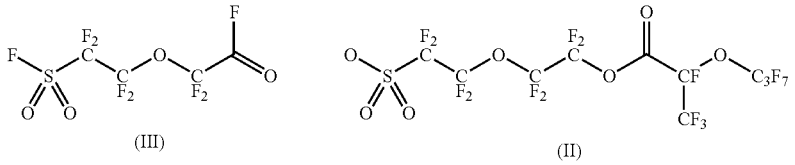

The compound V having a $FSO_2$— group in its terminal structure, can be synthesized by fluorinating a compound having a $ClSO_2$— group in its terminal structure by means of potassium fluoride. Otherwise, the compound V may be synthesized also by reacting the following compound Va with $SO_2Cl$ to form the following compound Vb, then fluorinating the compound Vb with potassium fluoride to form the following compound Vc, and further, reacting the compound Vc with the following compound Vd.

$NaOSO_2(CH_2)_2OH$ (Va)

$ClSO_2(CH_2)_2Cl$ (Vb)

$FSO_2(CH_2)_2Cl$ (Vc)

$NaO(CH_2)_2OH$ (Vd)

As a second embodiment of the above continuous process, the following reactions employing compounds 1b to 6b may be mentioned. Namely, it is a continuous process wherein the following compound 1b is reacted with the following compound 6b to form the following compound 3b, then, the compound 3b is reacted with fluorine in a liquid phase to form the following compound 4b, further, the compound 4b is decomposed to obtain not only the following compound 5b but also the compound 6b, and at least a part of the compound 6b is reacted with the compound 1b.

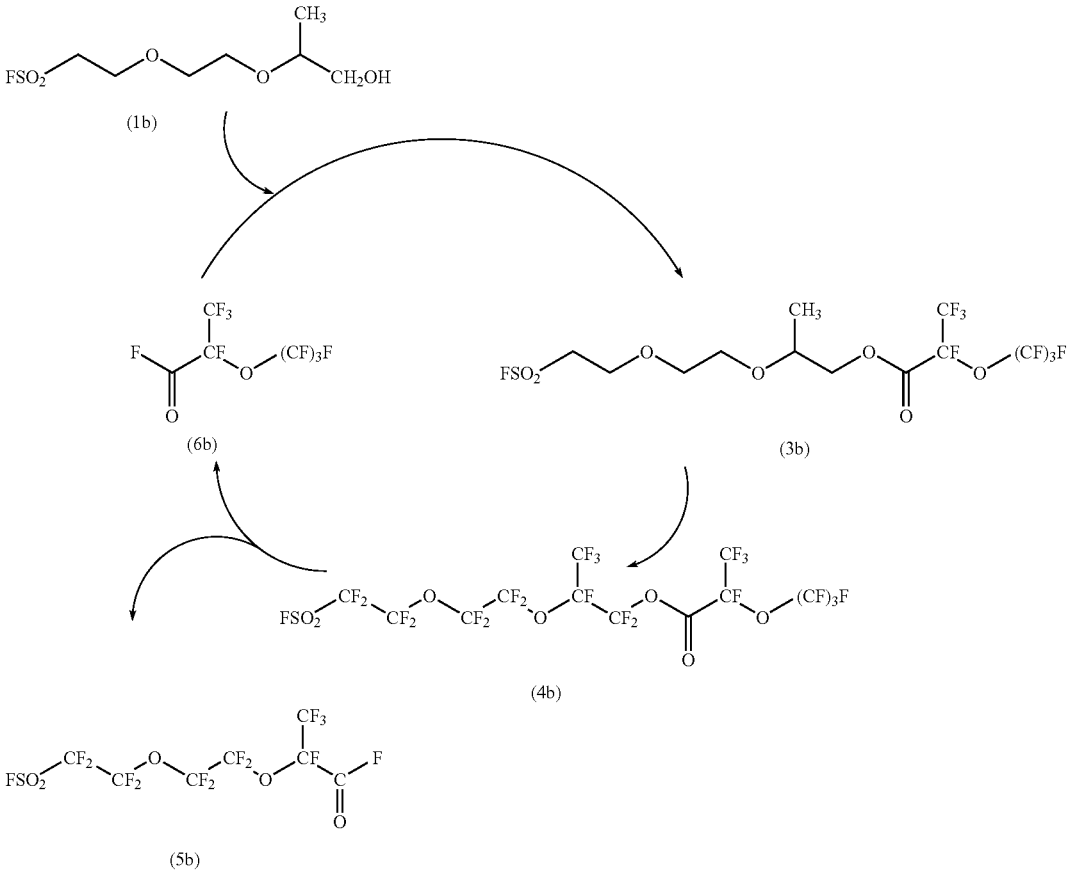

The compound 5b can also be prepared by a method of reacting the compound III-obtained in the first embodiment, with HFPO. Like the compound 5b, a compound essentially having a partial structure of "$C^1F—C^2—COF$" at its molecular terminal (hereinafter referred to as "the specific terminal fluorine atom-containing sulfonyl fluoride compound"), can be converted so that the molecular terminal is changed to "$C^1=C^2$", by a pyrolytic reaction (for example, the method disclosed in Methods of Organic Chemistry, 4, Vol. 10b, Part 1, pp. 703). From the compound 5b obtained by such a method, the following compound A which is useful as a monomer for the synthesis of ion-exchange membranes, can be produced.

(III)

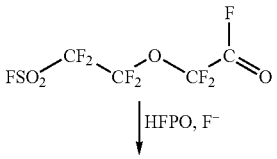

(5b)

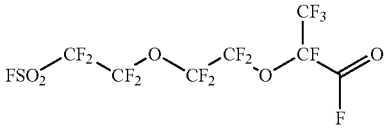

-continued (A)

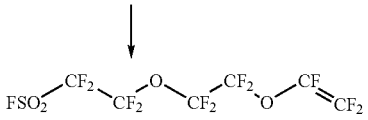

The pyrolytic reaction to obtain the unsaturated compound (hereinafter referred to as "the fluorine atom-containing sulfonyl fluoride vinyl ether") represented by the compound A from the specific terminal, fluorine atom-containing sulfonyl fluoride compound represented by the compound 5b, may, for example, be a gas phase pyrolytic reaction of the specific terminal fluorine atom-containing sulfonyl fluoride compound, or a pyrolytic reaction of an alkali salt of a carboxylic acid obtained by the reaction of the specific terminal fluorine atom-containing sulfonyl fluoride compound with an alkali metal hydroxide.

The reaction temperature in the gas phase pyrolytic reaction of the specific terminal fluorine atom-containing sulfonyl fluoride compound is preferably from 250 to 400° C., more preferably from 250 to 350° C. Further, the reaction temperature in the pyrolytic reaction of the above alkali salt of a carboxylic acid is preferably from 150 to 350° C., more preferably from 200 to 280° C. If the reaction temperature in the gas phase pyrolytic reaction is less than 250° C., or if the reaction temperature in the pyrolytic reaction of the alkali salt of a carboxylic acid is less than 150° C., the conversion to the fluorine atom-containing sulfonyl fluoride vinyl ether tends to be low, and if the reaction temperature in the gas phase pyrolytic reaction exceeds 400° C., or if the reaction temperature in the pyrolytic reaction of the alkali salt of a carboxylic acid exceeds 350° C., the specific terminal fluorine atom-containing sulfonyl fluoride compound tends to be hardly pyrolized to the fluorine atom-containing sulfonyl fluoride vinyl ether, and pyrolysates other than the fluorine atom-containing sulfonyl fluoride vinyl ether tend to increase.

The gas phase pyrolytic reaction of the specific terminal fluorine atom-containing sulfonyl fluoride compound is preferably carried out by a continuous reaction. The continuous reaction is preferably carried out by a method wherein a vaporized specific terminal fluorine atom-containing sulfonyl fluoride compound is passed through a heated reaction tube, the formed fluorosulfonyl fluoride vinyl ether is obtained as a discharge gas, which is condensed and continuously recovered. In a case where the pyrolytic reaction is carried out in a gas phase, it is preferred to employ a tubular reactor. When the tubular reactor is employed, the space time is preferably from 0.1 second to 10 minutes on the basis of superficial velocity. The pressure of the reaction is not particularly limited. Further, when the specific terminal fluorine atom-containing sulfonyl fluoride compound is a high boiling compound, it is preferred to carry out the reaction under reduced pressure. Especially when the specific terminal fluorine atom-containing sulfonyl fluoride compound is a low boiling point compound, as decomposition of the product will be suppressed and the conversion will be high, it is preferred to carry out the reaction under pressure.

In a case where the gas phase pyrolytic reaction is carried out by means of a tubular reactor, it is preferred to pack glass, an alkali metal salt, or an alkaline earth metal salt into the reactor for the purpose of accelerating the reaction. As the alkali metal salt or the alkali earth metal salt, a carbonate or a fluoride is preferred. As the glass, common soda glass may be mentioned, and glass bead formed into a bead shape and having improved flowability, are particularly preferred. The alkali metal salt may, for example, be sodium carbonate, sodium fluoride, potassium carbonate, or lithium carbonate. The alkaline earth metal salt may, for example, be calcium carbonate, calcium fluoride, or magnesium carbonate. Further, in a case where the glass, the alkali metal salt, or the alkaline earth metal salt, is to be packed into the reaction tube, it is particularly preferred to employ glass beads or light ash of sodium carbonate having a particle size of from about 100 to 250 μm, whereby a reaction system of a fluidized layer type may be employed.

In the gas phase pyrolytic reaction, it is preferred to carry out the reaction in the presence of an inert gas which is not directly involved in the pyrolytic reaction, for the purpose of accelerating the vaporization of the specific terminal fluorine atom-containing sulfonyl fluoride compound. As such an inert gas, nitrogen, carbon dioxide, helium or argon may, for example, be mentioned. The amount of the inert gas is preferably from about 0.01 to 50 vol %, based on the specific terminal fluorine atom-containing sulfonyl fluoride compound. If the amount of the inert gas is too large, the recovery of the product tends to be low, such being undesirable. On the other hand, in a case where the boiling point of the specific terminal fluorine atom-containing sulfonyl fluoride compound is high, the pyrolysis can be carried out by a liquid phase reaction.

As described above, according to the process of the present invention, it is unnecessary to employ a perfluoroalkylene ether in the preparation of a fluorine atom-containing sulfonyl fluoride compound, whereby the safety in the preparation can be increased, and sulfonyl fluoride compounds having various structures (compound 1, compound 1a, compound V, compound 1b, etc.) can be produced at a relatively low cost. Further, the process of the present invention can be a continuous process, and further, the compound 4a as a reaction product, can be re-used as the solvent 2 to be used for the reaction of the compound 3a with fluorine in a liquid phase, whereby the amount of the materials at the time of the preparation and the amount of waste can be reduced, and the fluorine atom-containing sulfonyl fluoride compound can be prepared very economically.

EXAMPLES

Now, the present invention will be described in detail with reference to Examples, but the present invention is by no means thereby restricted. In the following, gas chromatography will be referred to as GC, and gas chromatography mass spectrometry will be referred to as GC-MS. Further, the purity determined from the peak area ratio of GC will be referred to as GC purity, the yield will be referred to as GC yield, and the yield obtained from the peak area ratio of the NMR spectrum will be referred to as NMR yield. Further, tetramethylsilane will be referred to as TMS, $CCl_2FCClF_2$ as R-113, and tetrahydrofuran as THF. Further, the NMR spectrum data are shown as being within an apparent chemical shift range. The standard value of the standard substance $CDCl_3$ in the $^{13}$C-NMR was 76.9 ppm. In the quantitative analysis by the $^{19}$F-NMR, $C_6F_6$ was used as the internal standard.

Example 1

Production of $FSO_2CH_2CH_2OCH_2CH_2OH$

Into a round flask, $HO(CH_2)_2OH$ (140.9 g) and a methanol solution of sodium methylate (28 wt %, 96.4 g) were charged and stirred, and heated under reduced pressure to distill off methanol thereby to obtain a solution of $HOCH_2CH_2ONa$. It was confirmed by GC that no methanol remained in the reaction solution. Into a four necked flask, $FSO_2CH_2CH_2Cl$ (50 g) and THF (100 mL) were charged and stirred under cooling with ice bath, and the previously obtained solution of $HOCH_2CH_2ONa$ was dropwise added thereto over a period of 2.5 hours, while maintaining the internal temperature to be at most 10° C. After completion of the dropwise addition, it was stirred at room temperature for 2 hours and then added to water (400 mL), and dichloromethane (183 g) was added. The obtained crude liquid was subjected to liquid separation, and the obtained aqueous layer was extracted with dichloromethane (124 g). The separated aqueous layer was further extracted with dichloromethane (126 g), and the organic layers were put together. It was dried over magnesium sulfate, and after filtration, the solvent was distilled off to obtain a crude product (47.1 g). The obtained crude liquid was used for the next step without carrying out purification.

$^1$H-NMR (300.4 MHz, $CDCl_3$, TMS) δ (ppm): 3.63 to 3.71 (m, 4H), 3.74 to 3.79(m, 2H), 3.99 to 4.05(m, 2H)

$^{19}$F-NMR (282.7 MHz, $CDCl_3$, $CFCl_3$) δ (ppm): 58.4 (1F).

Example 2

Production of $FSO_2CH_2CH_2OCH_2CH_2OCOCF(CF_3)OCF_2CF_2CF_3$(esterification step)

$FSO_2CH_2CH_2OCH_2CH_2OH$ (47.1 g) having a purity of 64%, obtained in Example 1, and triethylamine (19.5 g) were put into a flask and stirred under cooling with ice bath. $FCOCF(CF_3)OCF_2CF_2CF_3$(64.1 g) was dropwise added thereto over a period of 40 minutes, while maintaining the internal temperature to be at most 10° C. After completion of the dropwise addition, it was stirred for two hours at room temperature and then added to ice water (100 mL).

The obtained crude liquid was subjected to liquid separation, and the lower layer was washed twice with water (100 mL) and dried over magnesium sulfate, followed by filtration to obtain a crude liquid. The crude liquid was purified by silica gel column chromatography (developing solvent: dichloropentafluoropropane (tradename: AK-225)) to obtain $FSO_2CH_2CH_2OCH_2CH_2OCOCF(CF_3)OCF_2CF_2CF_3$ (21.2 g). The GC purity was 88%.

$^1$H-NMR (300.4 MHz, $CDCl_3$, TMS) δ (ppm): 3.57 to 3.63 (m, 2H), 3.81(t, J=4.5 Hz, 2H), 3.95 to 4.00(m, 2H), 4.48 to 4.60(m, 2H)

$^{19}$F-NMR (282.7 MHz, $CDCl_3$, $CFCl_3$) δ (ppm): 58.2 (1F), −79.8(1F), −81.3(3F), −82.1(3F), −86.6(1F), −129.4 (2F), −131.5(1F).

Example 3

Production of $FSO_2CF_2CF_2OCF_2CF_2OCOCF(CF_3)OCF_2CF_2CF_3$(fluorination step)

Into a 500 mL autoclave made of nickel, R-113(313 g) was added, stirred and maintained at 25° C. At the gas outlet of the autoclaves a cooler maintained at 20° C., a packed layer of NaF pellets and a cooler maintained at −10° C., were installed in series. Further, a liquid-returning line was installed to return a condensed liquid from the cooler maintained at −10° C. to the autoclave. After supplying nitrogen gas for 1.0 hour, fluorine gas diluted to 20% by nitrogen gas (hereinafter referred to as diluted fluorine gas) was supplied for one hour at a flow rate of 7.78 L/hr. Then, while supplying the diluted fluorine gas at the same flow rate, a solution obtained by dissolving $FSO_2CH_2CH_2OCH_2CH_2OCOCF(CF_3)OCF_2CF_2CF_3$ (7.01 g) obtained in Example 2, in R-113(140 g), was supplied over a period of 5.5 hours.

Then, while supplying the diluted fluorine gas at the same flow rate and maintaining the pressure of the reactor to be 0.15 MPa, a R-113 solution having a benzene concentration of 0.01 g/mL, was supplied (6 mL) while raising the temperature from 25° C. to 40° C. And the benzene inlet of the autoclave was closed and stirring was continued for 0.3 hour. Then, while maintaining the pressure of the reactor to be 0.15 MPa and the internal temperature of the reactor to be 40° C., the above-mentioned benzene solution (6 mL) was supplied, and stirring was continued for 0.3 hour. Further, the same operation was repeated three times. The total amount of benzene supplied, was 0.31 g, and the total amount of R-113 supplied was 30 mL. Further, nitrogen gas was supplied for 1.0 hour. The desired product was quantitatively analyzed (internal standard: C6F6) by $^{19}$F-NMR, whereby the yield of the above identified compound was 84%.

$^{19}$F-NMR (376.0 MHz, $CDCl_3$, $CFCl_3$) δ (ppm): 45.2 (1F), −79.9(1F), −82.0(3F), −82.2(3F), −82.6(2F), −87.0 (1F), −88.5(2F), −92.3(2F), −112.9(2F), −130.2(2F), −132.1 (1F).

Example 4

Production of $FSO_2CF_2CF_2OCF_2COF$ (decomposition step)

$FSO_2CF_2CF_2OCF_2CF_2OCOCF(CF_3)OCF_2CF_2CF_3$(3.1 g) obtained in Example 3 was charged into a flask together with NaF powder (0.02 g) and heated at 140° C. for 10 hours in an oil bath with vigorous stirring. At the upper portion of the flask, a reflux condenser having the temperature adjusted at 20° C., was installed. After cooling, the liquid sample (3.0 g) was recovered. As a result of the analysis by GC-MS, $CF_3CF(OCF_2CF_2CF_3)COF$ and $FSO_2CF_2CF_2OCF_2COF$ were confirmed to be the main products, and the NMR yield was 71.2%. Further, $FCOCF(CF_3)OCF_2CF_2CF_3$ was obtained in a yield of 74.0%.

Example 5

Recycling of $FCOCF(CF_3)OCF_2CF_2CF_3$(continuous process)

$FCOCF(CF_3)OCF_2CF_2CF_3$ obtained in Example 4 was reacted with $FSO_2CH_2CH_2OCH_2CH_2OH$ under the same conditions as in the above esterification to obtain $FSO_2CH_2CH_2OCH_2CH_2OCOCF(CF_3)OCF_2CF_2CF_3$. The obtained $FSO_2CH_2CH_2OCH_2CH_2OCOCF(CF_3)OCF_2CF_2CF_3$ was fluorinated under the same conditions as in the above fluorination step to obtain $FSO_2CF_2CF_2OCF_2CF_2OCOCF(CF_3)OCF_2CF_2CF_3$. The obtained $FSO_2CF_2CF_2OCF_2CF_2OCOCF(CF_3)OCF_2CF_2CF_3$ was decomposed under the same conditions as in the above decomposition step to obtain $FSO_2CF_2CF_2OCF_2COF$ and $FCOCF(CF_3)OCF_2CF_2CF_3$.

INDUSTRIAL APPLICABILITY

According to the present invention, a process can be presented whereby fluorine atom-containing sulfonyl fluoride compounds having various molecular structures can be produced efficiently and at low costs and whereby the difficulties in the production are solved.

The entire disclosure of Japanese Patent Application No. 2000-361450 filed on Nov. 28, 2000 including specification, claims and summary is incorporated herein by reference in its entirety.

What is claimed is:

[1. A process for producing a fluorine atom-containing sulfonyl fluoride compound, which comprises reacting a compound of the following formula (1) with a compound of the following formula (2) to form a compound of the formula (3), then, reacting the compound of the formula (3) with fluorine in a liquid phase to form a compound of the following formula (4), and further, decomposing the compound of the formula (4) to obtain a compound of the following formula (5):

$$XSO_2R^A\text{-}E^1 \quad (1)$$

$$R^B\text{-}E^2 \quad (2)$$

$$XSO_2R^A\text{-}E\text{-}R^B \quad (3)$$

$$FSO_2R^{AF}\text{-}E^F\text{-}R^{BF} \quad (4)$$

$$FSO_2R^{AF}\text{-}E^{F1} \quad (5)$$

wherein $R^A$ is a bivalent organic group, $E^1$ is a monovalent reactive group, $R^B$ is a monovalent organic group, $E^2$ is a monovalent reactive group which is reactive with $E^1$, E is a bivalent connecting group formed by the reaction of $E^1$, with $E^2$, $R^{AF}$ is the same group as $R^A$, or a bivalent organic group formed by the fluorination of $R^A$, $R^{BF}$ is the same group as $R^B$, or a monovalent organic group formed by the fluorination of $R^B$, $E^F$ is the same group as E, or a bivalent connecting group formed by the fluorination of E, $E^{F1}$ is a monovalent group formed by the decomposition of $E^F$, and X is a halogen atom, provided that at least one of $R^A$, $R^B$ and E is a group which can be fluorinated, and at least one of $R_{AF}$, $R^{BF}$ and $E^F$ is a group formed by the fluorination of $R^A$, $R^B$ and E, respectively.]

[2. The process for producing a fluorine atom-containing sulfonyl fluoride compound according to claim 1, wherein X is a fluorine atom.]

[3. The process for-producing a fluorine atom-containing sulfonyl fluoride compound according to claim 1, wherein the fluorine content in the compound of the formula (3) is at least 30 mass %.]

[4. The process for producing a fluorine atom-containing sulfonyl fluoride compound according to claim 1, wherein the molecular weight of the compound of the formula (3) is from 200 to 1,000.]

[5. The process for producing a fluorine atom-containing sulfonyl fluoride compound according to claim 1, wherein $R^{AF}$ is a bivalent organic group selected from the group consisting of a perfluoro bivalent saturated hydrocarbon group, a perfluoro(partially halogeno bivalent saturated hydrocarbon) group, a perfluoro(hetero atom-containing bivalent saturated hydrocarbon) group, and a perfluoro (partially halogeno(hetero atom-containing bivalent saturated hydrocarbon)) group, and $R^{BF}$ is a monovalent organic group selected from the group consisting of a perfluoro monovalent saturated hydrocarbon group, a perfluoro (partially halogeno monovalent saturated hydrocarbon) group, a perfluoro(hetero atom-containing monovalent saturated hydrocarbon) group, and a perfluoro(partially halogeno(hetero atom-containing monovalent saturated hydrocarbon)) group.]

[6. The process for producing a fluorine atom-containing sulfonyl fluoride compound according to claim 1, wherein the compound of the formula (4) is decomposed to obtain not only the compound of the formula (5), but also a compound of the following formula (6):

$$R^{BF}\text{-}E^{F2} \tag{6}$$

wherein $E^{F2}$ is a monovalent group formed by the decomposition of $E^F$, which may be the same as or different from $E^{F1}$, and $R^{BF}$ is as defined above.]

[7. The process for producing a fluorine atom-containing sulfonyl fluoride compound according to claim 1, wherein the compound of the formula (1) is a compound of the following formula (1a), the compound of the formula (2) is a compound of the following formula (2a), the compound of the formula (3) is a compound of the following formula (3a), the compound of the formula (4) is a compound of the following formula (4a), and the compound of the formula (5) is a compound of the following formula (5a):

$$XSO_2R^A\text{—}CH_2OH \tag{1a}$$

$$R^B\text{—}COY \tag{2a}$$

$$XSO_2R^A\text{—}CH_2OCO\text{—}R^B \tag{3a}$$

$$FSO_2R^{AF}\text{—}CF_2OCO\text{—}R^{BF} \tag{4a}$$

$$FSO_2R^{AF}\text{—}COF \tag{5a}$$

wherein Y is a halogen atom which is the same as or different from X, and $R^A$, $R^B$, $R^{AF}$ and $R^{BF}$ are as defined above.]

[8. The process for producing a fluorine atom-containing sulfonyl fluoride compound according to claim 7, wherein the compound of the formula (4a) is decomposed to obtain not only the compound of the formula (5a), but also a compound of the following formula (6a):

$$R^{BF}\text{—}COF \tag{6a}$$

wherein $R^{BF}$ is as defined above.]

[9. The process for producing a fluorine atom-containing sulfonyl fluoride compound according to claim 8, wherein the compound of the formula (2a) has the same structure as the compound of the formula (6a), and at least a part of the compound of the formula (6a) obtained from the reaction product obtained by the decomposition of the compound of the formula (4a), is used as at least a part of the compound of the formula (2a) to react with the compound of the formula (1a), to continuously obtain the compound of the formula (5a).]

*10. A compound of the following formula (3a):*

$$XSO_2R^A\text{—}CH_2OC(O)\text{—}R^{BF} \tag{3a}$$

*wherein*

*$R^A$ is a saturated hydrocarbon group, a partially halogeno bivalent saturated hydrocarbon group, a hetero atom-containing bivalent saturated hydrocarbon group, and a partially halogeno(hetero atom-containing bivalent saturated hydrocarbon)) group;*

*$R^{BF}$ is a monovalent organic group selected from the group consisting of a perfluoro monovalent saturated hydrocarbon group, a perfluoro(partially halogeno monovalent saturated hydrocarbon) group, a perfluoro (hetero atom-containing monovalent saturated hydrocarbon) group, and a perfluoro(partially halogeno(hetero atom-containing monovalent saturated hydrocarbon)) group; and*

*X is Cl or F, and*

*wherein said hetero atom-containing group, monovalent or divalent, is group containing a hetero atom selected from the group consisting of oxygen atom, nitrogen atom, and sulfur atom, or said hetero atom-containing group, monovalent or divalent, is —C—C(=O)—C— or —C—$SO_2$—C—.*

*11. The compound according to claim 10, wherein $R^A$ is $C_{1-10}$ alkylene group or $C_{1-20}$ etheric oxygen atom-containing alkylene group.*

*12. The compound according to claim 10, wherein $R^{BF}$ is a perfluoro monovalent saturated hydrocarbon group or a perfluoro(hetero atom-containing monovalent saturated hydrocarbon) group.*

*13. The compound according to claim 10, wherein X is a fluorine atom.*

* * * * *

UNITED STATES PATENT AND TRADEMARK OFFICE

CERTIFICATE OF CORRECTION

PATENT NO. : RE 41,184 E
APPLICATION NO. : 12/234109
DATED : March 30, 2010
INVENTOR(S) : Ito et al.

It is certified that error appears in the above-identified patent and that said Letters Patent is hereby corrected as shown below:

On the title page, Item (*) Notice

Delete

"This patent is subject to a terminal disclaimer.".

Signed and Sealed this

Fifteenth Day of June, 2010

David J. Kappos

David J. Kappos
*Director of the United States Patent and Trademark Office*